United States Patent
Birchard

(10) Patent No.: US 10,234,897 B2
(45) Date of Patent: Mar. 19, 2019

(54) CATHETER-BASED SYSTEM HAVING DONGLE WITH SHAPE MEMORY

(71) Applicant: BIOSENSE WEBSTER (ISRAEL) LTD., Yokneam (IL)

(72) Inventor: Christopher J. Birchard, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/646,015

(22) Filed: Jul. 10, 2017

(65) Prior Publication Data

US 2017/0371369 A1      Dec. 28, 2017

Related U.S. Application Data

(63) Continuation of application No. 13/826,545, filed on Mar. 14, 2013, now Pat. No. 9,703,317.

(51) Int. Cl.
*G06F 1/16* (2006.01)
*A61B 34/20* (2016.01)
(Continued)

(52) U.S. Cl.
CPC ............ *G06F 1/16* (2013.01); *A61B 18/1492* (2013.01); *A61B 34/20* (2016.02); *A61B 2018/00178* (2013.01)

(58) Field of Classification Search
CPC ....... G06F 1/16; A61B 19/00; A61B 19/5244; A61B 18/00; A61B 18/14; A61B 18/1492; A61B 2018/00178
See application file for complete search history.

(56) References Cited

U.S. PATENT DOCUMENTS

| 1,218,570 A | 3/1917 | Koch |
| 1,810,439 A | 6/1931 | Rollman |

(Continued)

FOREIGN PATENT DOCUMENTS

| EP | 1 169 974 A1 | 1/2002 |
| JP | 2001-501122 A | 1/2001 |

(Continued)

OTHER PUBLICATIONS

Extended European Search Report dated Oct. 28, 2014 for EP Application No. 14159366.5, 8 pgs.

(Continued)

*Primary Examiner* — Edwin A. Leon
*Assistant Examiner* — Oscar Jimenez
(74) *Attorney, Agent, or Firm* — Lewis Roca Rothgerber Christie LLP

(57) ABSTRACT

A dongle couples an electrophysiologic catheter and a navigational system, including a patient interface unit (PIU). The dongle permits hardware normally carried on catheter control handle to be relocated onto the dongle to render catheter "greener" and less costly to manufacture use. The dongle having a support portion with flexibility, shape memory and/or varying degrees of stiffness also advantageously allows a user more control over the placement, position and orientation of the dongle. The dongle has a body with a first electrical interface unit, and a support portion with a second electrical interface unit, the support portion having an outer flexible tubular member with shape memory. In one embodiment, the support portion comprises a gooseneck tubing. In another embodiment, the support portion comprises a coiled spring.

20 Claims, 5 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 2,101,713 A | 12/1937 | Jolliffe | |
| 2,178,621 A | 11/1939 | Andre | |
| 2,724,736 A | 11/1955 | Klumpp, Jr. | |
| 2,971,178 A | 2/1961 | Reesby | |
| 4,753,223 A * | 6/1988 | Bremer | A61B 1/0058 |
| | | | 600/140 |
| 4,815,471 A | 3/1989 | Stobie | |
| 5,118,907 A | 6/1992 | Stout et al. | |
| 5,163,445 A * | 11/1992 | Christian | A61B 8/06 |
| | | | 248/623 |
| 5,397,304 A | 3/1995 | Truckai | |
| 5,507,787 A * | 4/1996 | Borghi | A61N 1/056 |
| | | | 439/909 |
| 5,607,094 A * | 3/1997 | Clark | A61B 17/072 |
| | | | 227/175.1 |
| 5,702,386 A | 12/1997 | Stern et al. | |
| 5,823,817 A | 10/1998 | Pyle | |
| 5,874,709 A | 2/1999 | New et al. | |
| 5,941,818 A * | 8/1999 | Hori | A61B 1/00073 |
| | | | 600/110 |
| 6,569,160 B1 * | 5/2003 | Goldin | A61B 18/12 |
| | | | 600/427 |
| 6,875,924 B2 | 4/2005 | Porter et al. | |
| 7,558,899 B2 | 7/2009 | Yip | |
| 9,662,169 B2 * | 5/2017 | Schultz | A61B 18/1492 |
| 9,703,317 B2 * | 7/2017 | Birchard | G06F 1/16 |
| 9,775,663 B2 * | 10/2017 | Blix | A61B 18/08 |
| 2002/0077665 A1 * | 6/2002 | Kordis | A61B 18/1492 |
| | | | 607/1 |
| 2003/0163052 A1 * | 8/2003 | Mott | A61B 5/0215 |
| | | | 600/486 |
| 2004/0078036 A1 * | 4/2004 | Keidar | A61B 18/1492 |
| | | | 606/41 |
| 2004/0082866 A1 * | 4/2004 | Mott | A61B 5/0215 |
| | | | 600/486 |
| 2007/0038056 A1 * | 2/2007 | Pappone | A61B 5/042 |
| | | | 600/374 |
| 2008/0140073 A1 * | 6/2008 | Schwartz | A61B 5/0422 |
| | | | 606/41 |
| 2008/0319314 A1 * | 12/2008 | Hill | A61B 18/1492 |
| | | | 600/424 |
| 2010/0273355 A1 * | 10/2010 | Gleason | A61B 1/00124 |
| | | | 439/638 |
| 2010/0273358 A1 | 10/2010 | von Malmborg et al. | |
| 2011/0015533 A1 | 1/2011 | Cox et al. | |
| 2011/0294358 A1 * | 12/2011 | Gleason | A61B 1/00124 |
| | | | 439/660 |
| 2011/0308835 A1 | 12/2011 | Piekny | |
| 2011/0312211 A1 | 12/2011 | Natoli | |
| 2012/0109118 A1 * | 5/2012 | Lalonde | A61N 1/403 |
| | | | 606/21 |
| 2013/0197555 A1 * | 8/2013 | Schaer | A61N 7/00 |
| | | | 606/170 |
| 2013/0296729 A1 * | 11/2013 | Datta | A61B 5/02 |
| | | | 600/515 |
| 2014/0276765 A1 * | 9/2014 | Blix | A61B 18/1206 |
| | | | 606/34 |
| 2014/0276771 A1 * | 9/2014 | Miller | A61B 18/1233 |
| | | | 606/34 |
| 2014/0316400 A1 * | 10/2014 | Blix | A61B 18/1206 |
| | | | 606/34 |
| 2015/0270634 A1 * | 9/2015 | Buesseler | H01R 13/02 |
| | | | 606/41 |
| 2015/0374435 A1 * | 12/2015 | Cao | A61B 18/1492 |
| | | | 606/34 |
| 2016/0235495 A1 * | 8/2016 | Wallace | A61B 18/1482 |
| 2016/0354134 A1 * | 12/2016 | Pageard | A61B 18/02 |
| 2017/0027640 A1 * | 2/2017 | Kunis | A61B 18/1492 |
| 2017/0348046 A1 * | 12/2017 | Beeckler | A61B 18/1492 |

FOREIGN PATENT DOCUMENTS

| | | |
|---|---|---|
| JP | 2001-520565 A | 10/2001 |
| JP | 2003-281943 | 10/2003 |
| WO | WO 98/14111 A1 | 4/1998 |
| WO | WO 99/40856 A1 | 8/1999 |

OTHER PUBLICATIONS

English translation of Notification of Reasons for Refusal, dated Nov. 21, 2017, issued in corresponding JP Application No. 2014-050110, 4 pages.

* cited by examiner

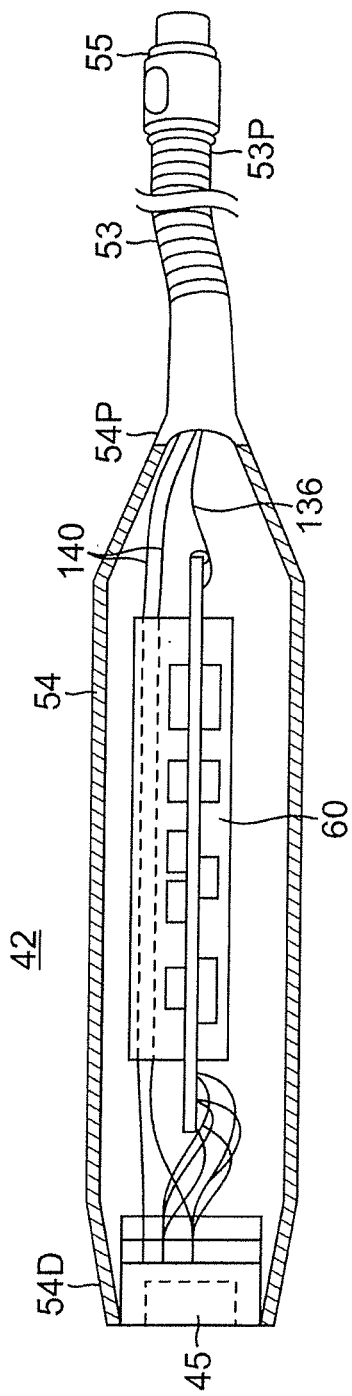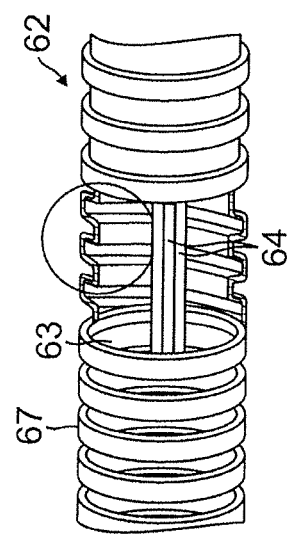

CATHETER-BASED SYSTEM HAVING DONGLE WITH SHAPE MEMORY

CROSS-REFERENCE TO RELATED APPLICATIONS

This application is a continuation of, and claims priority to and the benefit of U.S. patent application Ser. No. 13/826,545 filed Mar. 14, 2013, now U.S. Pat. No. 9,703,317, titled DONGLE WITH SHAPE MEMORY, the entire content of which is incorporated herein by reference.

FIELD OF INVENTION

The present invention relates to a dongle for coupling an electrophysiologic catheter with a patient interface unit.

BACKGROUND OF INVENTION

Catheterization is used in diagnostic and therapeutic procedures. For example, a cardiac catheter is used for mapping and ablation in the heart to treat a variety of cardiac ailments, including cardiac arrhythmias, such as atrial flutter and atrial fibrillation which persist as common and dangerous medical ailments, especially in the aging population. Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electroanatomical navigation systems (ENS) are used in conjunction with cardiac diagnostic and therapeutic catheters. One such system is CARTO available from Biosense Webster of Irwindale, Calif., which is a 3-D mapping system that provides electrophysiologists with magnetic location technology and visualization data of catheter tip and curve location, anatomical mapping with rapid creation of high-resolution, CT-like maps, and a patient interface unit (PIU) as a central connection for catheters and equipment.

Catheters for use with navigation systems have control handles which carry hardware, such as one or more printed circuit boards (PCB). For example, where electromagnetic sensor location data is transmitted via a sensor cable extending through the catheter, one or more circuit boards housed in the control handle may amplify the signals and convert them to a computer readable form before the data is transmitted to a signal processing unit of the navigation system. Although catheter handles are costly, catheters are not easily sterilized so they are intended for single use only and are discarded along with their hardware/metal bearing handles.

Dongles are known. They are pieces of hardware that attach to a computer or other electronic device and enable additional functions. Dongles typically include at least one interface plug for connection to the computer or other electronic device to enable electrical connection with the same. The dongle may include a flexible cable with a second interface plug.

With rising medical costs and the move toward more environmentally-friendly ("greener") catheters, current catheters are designed with the desire to relocate electronic hardware from the control handles to elsewhere in the PIU or other components of the navigation system. Some hardware may be relocated to a temporary location, such as a dongle, before finding a more permanent location within the navigation system. In that regard, a free-hanging dongle or a dongle with a flexible cable can be difficult to manage, especially as more dongles are used to temporarily house more components. A free-hanging dongle or one with a flexible cable may be prone to damage if knocked or bumped against other equipment and cause additional tension on any extension cable between the dongle and the catheter. Moreover, a free-hanging dongle or one with a flexible cable may be a nuisance to users who resort to using tape or zip-ties to secure or position them.

Accordingly, there is a desire for a catheter dongle with a stiffening member that would enable a user to better position and secure the dongle. There is also a desire for a catheter dongle that is more durable and less prone to damage from accidental bumping and adding stress or tension to catheter extension cables.

SUMMARY OF THE INVENTION

The present invention is directed to a dongle for coupling an electrophysiologic catheter and a navigational system, including a patient interface unit (PIU). The dongle permits some of the hardware normally carried on the catheter control handle to be relocated so that the catheter—normally intended for single use—is less costly to manufacture and contain less waste when discarded. The dongle having a support portion with flexibility, shape memory and/or varying degrees of stiffness also advantageously allows a user more control over the placement, position and orientation of the dongle. The support portion protects both the dongle body, as well as the catheter and the PIU by providing elastic displacement for shock absorption where the dongle or the catheter are accidentally bumped. The support portion also decreases the amount of stress and tension imposed on any extension cable that is connecting the catheter to the dongle.

In one embodiment, the dongle has a body with a first electrical interface unit, and a support portion with a second electrical interface unit, the support portion having an outer flexible tubular member with shape memory. In one embodiment, the support portion comprises a gooseneck tubing. In another embodiment, the support portion comprises a coiled spring.

In a more detailed embodiment, the electrical interface unit may comprises an electrical connection port or an electrical plug adapted to transmit electrical signals, where the electrical signals may comprise electrical signals are representative of electrical activity in a patient's body, position data of a distal portion of the catheter within a patient's body, and/or RF energy.

In a more detailed embodiment, the body of the dongle houses components that may be typically found in a catheter control handle, such as electronic hardware, including printed circuit boards which may be used to process electrical signals representative of position data of a distal portion of the catheter within a patient's body.

BRIEF DESCRIPTION OF THE DRAWINGS

These and other features and advantages of the present invention will be better understood by reference to the following detailed description when considered in conjunction with the accompanying drawings wherein:

FIG. 4 is a side cross-sectional view of a dongle, in accordance with an embodiment of the present invention.

FIG. 5 is a side view of one embodiment of a flexible cable or gooseneck, shown partially broken away.

DETAILED DESCRIPTION OF THE INVENTION

Figure 1:
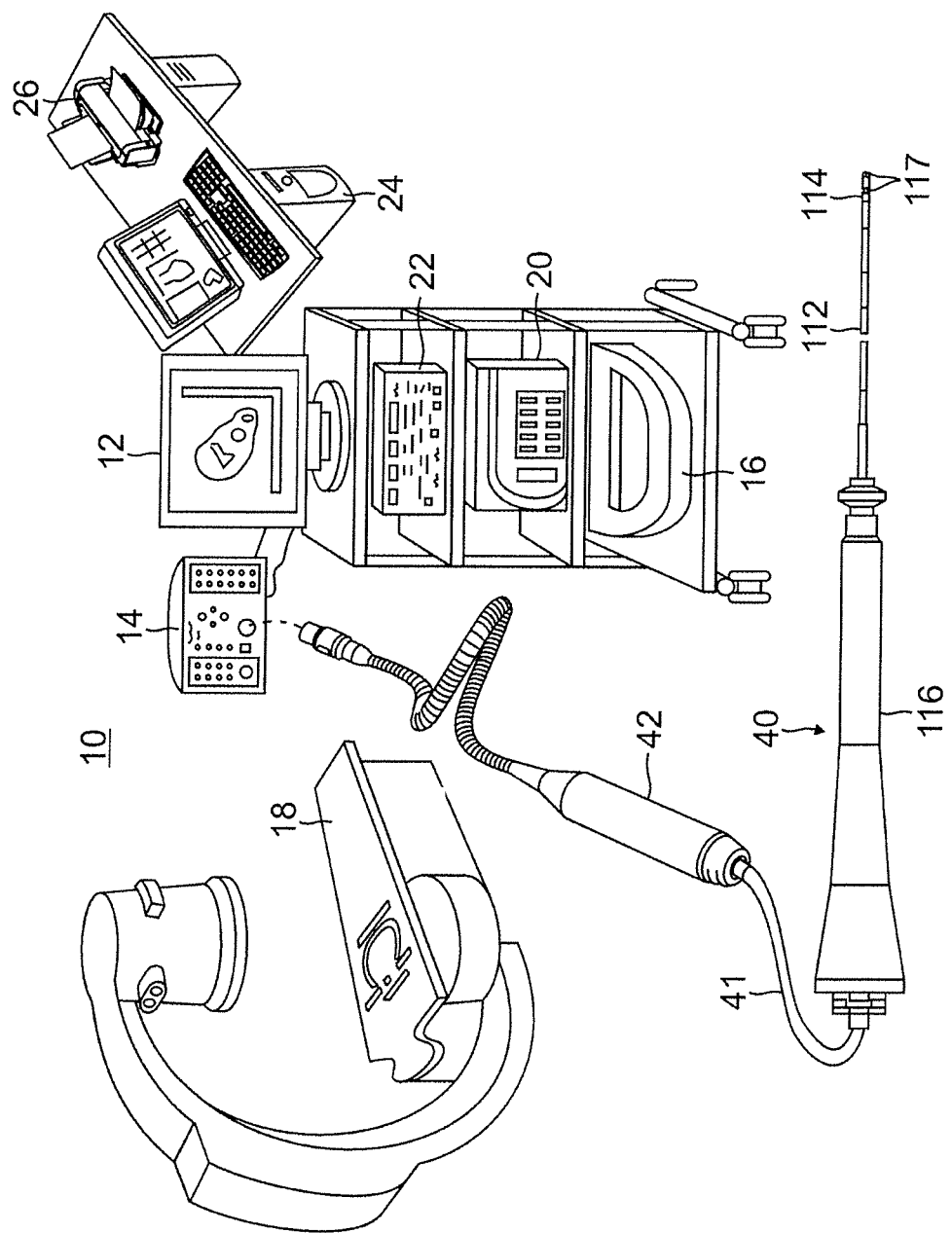
FIG. 1 is pictorial of a catheter-based electroanatomical navigation system using a dongle, in accordance with an embodiment of the present invention.
Figure 2:
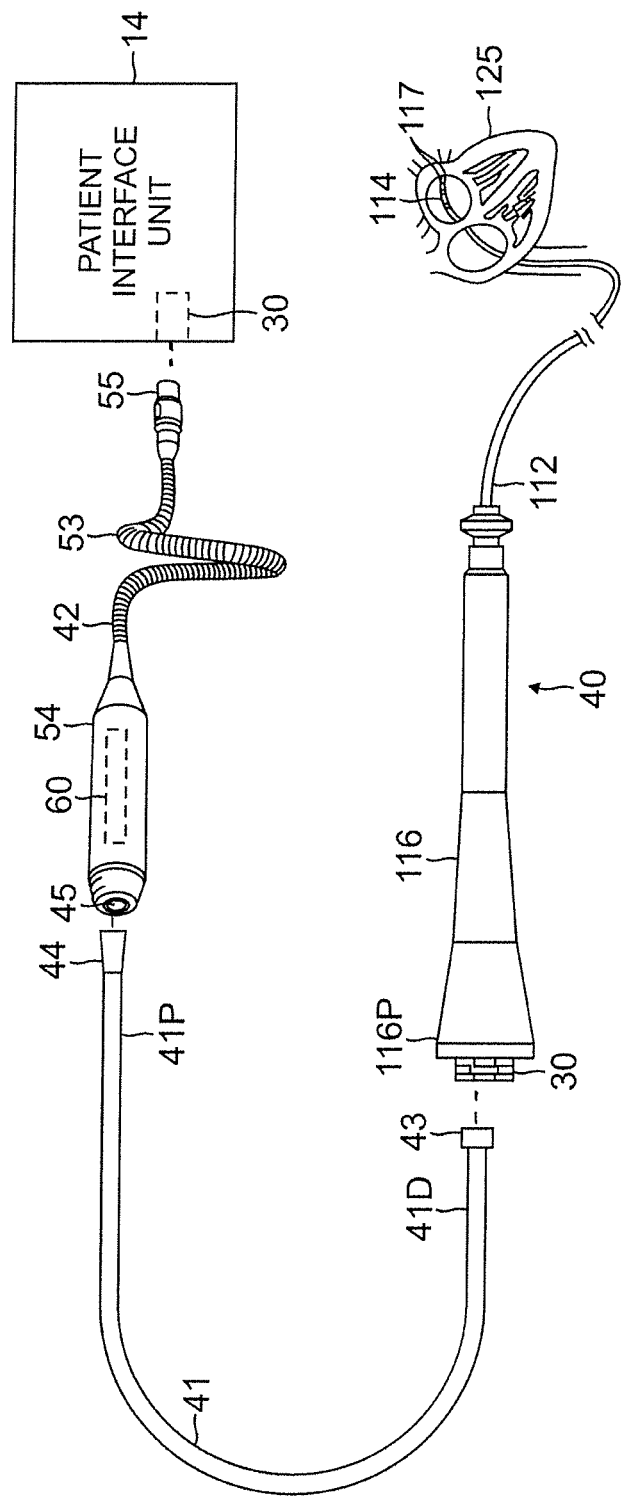
FIG. 2 is a schematic pictorial of the catheter-based electroanatomical navigation system of FIG. 1, in use in a cardiac procedure.

With reference to FIG. 1, a catheter-based electroanatomical navigation system 10 is shown for use with a catheter 40, an extension cable 41 and a dongle 42, in accordance with the present invention. The system 10 includes at least one monitor 12, a patient interface unit (PIU) 14, a location pad 16, a signal processing unit 20, an ablation energy generator 22, a workstation 24 and a printer 26. The monitor 12 displays patient data and maps. The PIU 14 allows cable connections between the signal processing unit 20 and all other system components. The location pad 16 is for placement under a patient lying on a patient table 18, enabling accurate detection of catheter location. The signal processing unit 20 determines all location and performs ECG calculations. The generator 22 may be an RF generator for supplying RF energy to the catheter. The workstation 24 is a computer adapted for storing patient data and maps. The printer 26 is provided to print color maps produced by the system 10. As shown in FIGS. 1 and 2, the dongle 42 extends between PIU 14 and the catheter 40, providing an electrical connection and performing any function(s) used or necessary for data gathered and transmitted by the catheter to be understood and processed by the system 10. Accordingly, the PIU 14 includes at least one electrical connection interface, for example, port 30 configured to interface with the catheter 40 via the dongle 42.

Figure 3:
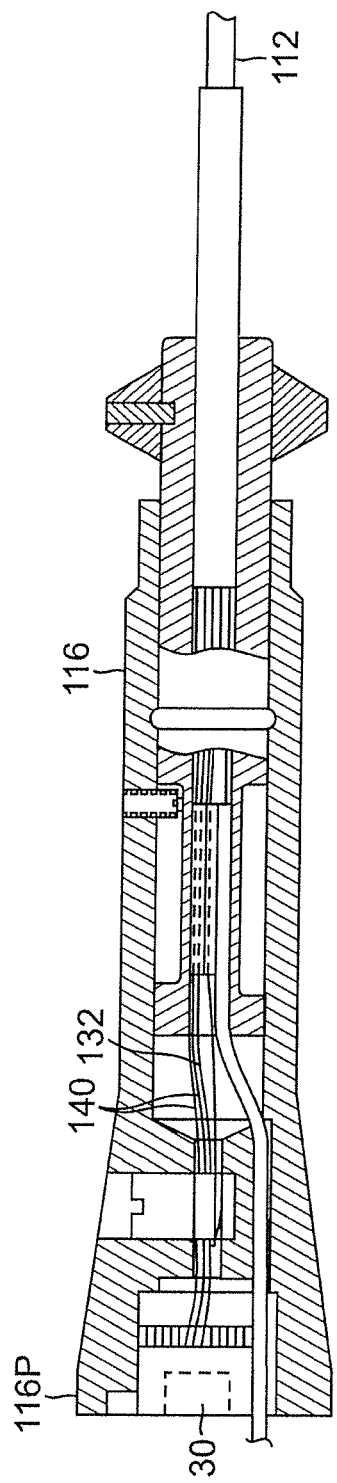
FIG. 3 is a side cross-sectional view of a catheter control handle, in accordance with an embodiment of the present invention.

In one embodiment, the catheter 40 has an elongated catheter body 112, a distal section 114 carrying tip and/or ring electrodes 117 and a control handle 116. As shown in FIG. 3, lead wires 140 are connected to the electrodes 117 for receiving and transmitting electronic signals for generating patient data, including 3-D anatomical maps of the patient's heart and ECG readings which are displayed on the monitor 14 and stored in the workstation 24. Moreover, electromagnetic position sensor(s) carried in the distal section 114 are responsive to external magnetic fields generated by the location pad 16 below the patient table 18 for generating electrical signals representative of the location of the distal tip section. Sensor cables 132 are connected from the position sensors to transmit these signals. Both the lead wires 140 and the sensor cables 132 extend through the length of the catheter, passing through the distal tip section 114, the catheter body 112 and the control handle 116. In that regard, a proximal end 116P of the control handle has at least one electrical connection port 30 to enable electrical connection with the lead wires 140 and sensor cables 132.

In one embodiment, the extension cable 41 between the catheter 40 and the dongle 42 has a proximal end 41P and a distal end 41D, as shown in FIG. 2. The distal end 41D is provided with a first interface, for example, plug 43 configured to be received in the electrical connection port 30 at the proximal end 116P of the control handle. The proximal end 41P is provided with a second interface, for example, plug 44 configured to be received in an electrical interface, for example, port 45 provided in a distal end of the dongle 42.

In one embodiment, the dongle 42 has a proximal support portion including a semi-rigid dongle cable 53, and an elongated distal body or housing 54 with a proximal end 54P, a distal end 54D and a generally sealed interior cavity extending therebetween, as shown in FIG. 4. At the distal end 54D, the electrical port 45 is configured to receive the second interface plug 44 of the extension cable 41. At a proximal end of the cable 53, an electrical interface, for example, plug 55 is configured to be received in the electrical port 30 of the PIU 14.

In the illustrated embodiment of FIG. 4, the dongle 42 houses hardware, for example, at least one printed circuit board (PCB) 60 which receives the electrical signals representative of catheter location transmitted by the sensor cables 136 to through the extension cable. The PCB 60 may amplify the signals and convert to a form readable by the signal processing unit 20 of the system 10 which are then transmitted via the proximal dongle cable 53.

Figure 6:
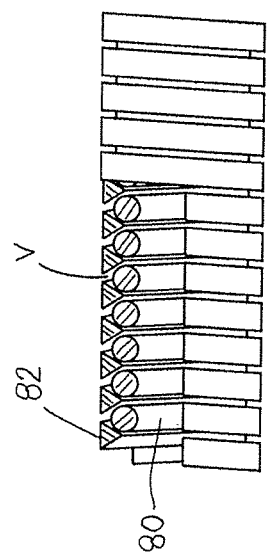
FIG. 6 is a side cross-sectional view of another embodiment of a flexible cable or gooseneck.
Figure 5A:
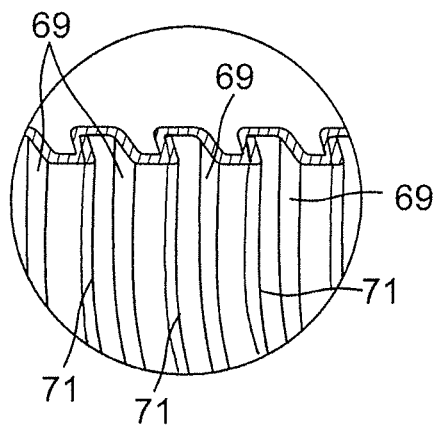
FIG. 5A is an enlarged detailed view of a portion of the flexible cable of FIG. 5.

With reference to FIGS. 5 and 6, the proximal cable 53 has an elongated flexible outer tubing member 62 defining a lumen 63 through which dongle wires 64 extend between the proximal and distal ends of the cable. In accordance with a feature of the present invention, the cable 53 is semi-rigid with shape memory so that the cable can be manipulated and configured by a user to selectively position or orient the dongle body 54 as desired. In one embodiment, the outer tubing member 62 comprises spirally wound flat strip(s) 67 of metal, metal alloy or generally rigid plastic material with longitudinal folds 69, interlocking adjacent longitudinal side edges 71 to form what is commonly referred to as a "gooseneck" tubular structure with a corrugated-like profile which provides flexibility and shape memory such that it can be manipulated into and retain a variety of desired configurations. The tubular structure may also act as a strain relief and/or a trunk cable insulation covering. The wires 64 extending through the tubing member 62 are protected and sealed within the tubing member 62.

FIG. 6 illustrates another embodiment of a flexible cable or gooseneck tubular structure comprising an inner coiled spring 80 and an outer sectional wire 82 wrapped around the coiled spring 80. In the illustrated embodiment, the underlying wire of the spring 80 has a circular cross-section and the outer sectional wire 82 has a triangular cross-section, wherein the underlying wire of the spring 80 is nested between two inner vertices V of adjacent pairs of sectional wires 82.

In use, the dongle 42 is connected to the PIU 14 via the connector plug 55 being received in the connector port 30, as shown in FIG. 2. A distal end of the dongle 42 receives the proximal connector 44 of the extension cable 41. The distal connector 43 of the extension cable 41 is received in the connector port 30 of the control handle 116. In a diagnostic procedure, as electrical signals are sensed by the tip and ring electrodes 117 on the distal tip section 114 of the catheter 40 positioned in patient's heart 125, the signals are transmitted via the lead wires 114 through the distal tip section 114, the catheter body 112 and the control handle 116. The signals are transmitted from the control handle 116 to the PIU 14 for processing by the signal processing unit 20 by the extension cable 41 and the dongle 42. In a therapeutic procedure, RF energy from the RF generator 22 of the system 10 is delivered to the tip and ring electrodes 117 via the PIU 14, the dongle 42, the extension cable, and the lead wires 140 extending through the control handle 116, the catheter body 112 and the distal tip section 114.

For position sensing of the catheter distal tip section 114 in the heart 125, electrical signals from the position sensors carried in the catheter distal tip section are transmitted via the sensor cables 132 which extends from the distal tip section, to the catheter body 12, and the control handle 116. The signals are further transmitted via the extension cable 41 to the dongle 42 which provides the PCB 60 that may amplify and/or convert the signals before transmitting them to the PIU 14 for processing by the signal processing unit 20 of the system 20.

Accordingly, the dongle of the present invention renders a catheter more disposable and "greener" by allowing expensive and metal-bearing hardware to be relocated from the catheter and onto the dongle. Moreover, the semi-rigid dongle of the present invention reduces the risk of damage to the dongle, the catheter and the navigation system by allowing the user more selection in the placement and positioning of the dongle.

Figure 7:
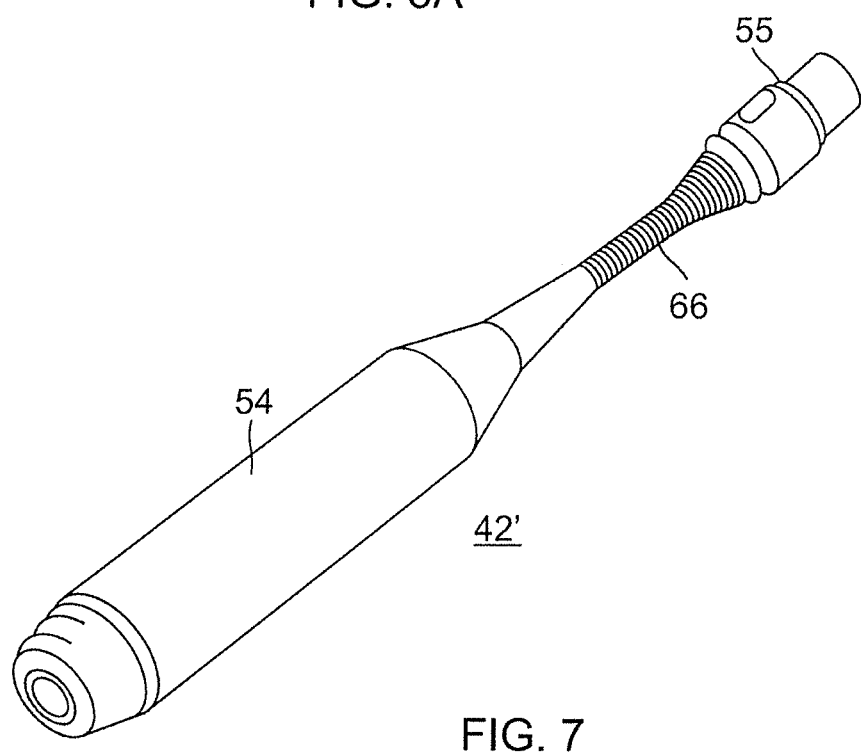
FIG. 7 is a side view of a dongle in accordance with another embodiment of the present invention.

In an alternate embodiment as shown in FIG. 7, a dongle 42' is illustrated with a proximal support portion including a semi-rigid dongle arm 66 whose proximal end carries the electrical plug 55. The arm 66 comprises a tightly coiled spring whose diameter may vary or be uniform throughout the length of the arm. The wires 64 extending through the spring are protected by the spring. The spring may be manufactured with different degrees of stiffness depending on the use and application, and be provided with a preformed shape. In the disclosed embodiment, the spring has sufficient stiffness to support the dongle body in a horizontal position but allows elastic bending or displacement where the dongle body is accidentally bumped.

It is understood by one of ordinary skill in the art that the body of the dongle may house a variety of electrical hardware for receiving and processing (including, for example, amplifying, converting, digitizing, etc.) a variety of electrical signals (including, for example, optical, audio, etc.) between the catheter and the navigation system, as needed or appropriate.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A system, comprising:
   a catheter comprising an elongated catheter body and a control handle at a proximal end of the catheter body;
   a signal processing unit;
   at least one monitor;
   a patient interface unit configured to connect the signal processing unit to the monitor; and
   a dongle configured to couple the control handle of the catheter to the patient interface unit, the dongle comprising:
      a dongle body having proximal and distal ends, the dongle body having a first electrical interface unit at its distal end configured for connection to a proximal end of the control handle; and
      a dongle support portion having proximal and distal ends and comprising an outer flexible tubular member with shape memory, the distal end of the dongle support portion being connected to the proximal end of the dongle body, the dongle support portion having a second electrical interface unit at its proximal end configured for connection to the patient interface unit.

2. The system of claim 1, wherein the dongle support portion comprises a gooseneck tubing.

3. The system of claim 1, wherein the dongle support portion comprises a coiled spring.

4. The system of claim 1, wherein the first electrical interface unit comprises an electrical connection port configured to receive an electrical plug.

5. The system of claim 1, wherein the second electrical interface unit comprises an electrical connection plug configured to be received in an electrical connection port.

6. The system of claim 1, wherein the first electrical interface unit is configured to receive electrical signals from the catheter.

7. The system of claim 6, wherein the electrical signals are representative of electrical activity in a patient's body.

8. The system of claim 6, wherein the electrical signals are representative of position data of a distal portion of the catheter within a patient's body.

9. The system of claim 1, wherein the first electrical interface unit is adapted to transmit RF energy to the catheter.

10. The system of claim 1, wherein the dongle body houses at least one printed circuit board.

11. The system of claim 10, wherein the at least one printed circuit board is configured to process electrical signals representative of position data of a distal portion of the catheter within a patient's body.

12. The system of claim 1, wherein the catheter further comprises a distal tip section carrying one or more electrodes and a lead wire for each of the one or more electrodes, each of the lead wires being configured to transmit electrical signals through the distal tip section, the catheter body and the control handle, and the control handle is configured to transmit the electrical signals to the signal processing unit through the dongle.

13. The system of claim 1, further comprising an extension cable configured to connect the dongle to the control handle of the catheter.

14. The system of claim 13, wherein the catheter further comprises a distal tip section carrying one or more electrodes and a lead wire for each of the one or more electrodes, each of the lead wires being configured to transmit electrical signals through the distal tip section, the catheter body and the control handle, and the control handle is configured to transmit the electrical signals to the signal processing unit through the extension cable and the dongle.

15. The system of claim 1, wherein the outer flexible tubular member of the dongle comprises at least one spirally wound flat strip.

16. The system of claim 1, wherein the outer flexible tubular member of the dongle comprises an inner coiled spring and an outer sectional wire wrapped around the inner coiled spring.

17. The system of claim 16, wherein each segment of the outer sectional wire comprises a triangular cross-section having an inner vertex, and wherein each segment of the inner coiled spring is nested between two inner vertices of two adjacent segments of the outer sectional wire.

18. The system of claim 1, wherein the outer flexible tubular member of the dongle comprises a coiled spring having an outer diameter that varies along a length of the dongle support portion.

19. The system of claim 1, wherein the patient interface unit is further configured to connect the dongle to the signal processing unit.

20. The system of claim 1, further comprising an ablation energy generator configured to supply ablation energy to the catheter through the dongle and the control handle.

\* \* \* \* \*